(12) United States Patent
Lombardo (10) Patent No.: US 11,191,672 B2
(45) Date of Patent: Dec. 7, 2021

(54) ZIPPER POUCH WITH INTEGRATED MOLDABLE SLEEPING MASK AND RETRACTABLE BEANIE

(71) Applicant: Lauren Lombardo, Staten Island, NY (US)

(72) Inventor: Lauren Lombardo, Staten Island, NY (US)

( * ) Notice: Subject to any disclaimer, the term of this patent is extended or adjusted under 35 U.S.C. 154(b) by 38 days.

(21) Appl. No.: 16/834,982

(22) Filed: Mar. 30, 2020

(65) Prior Publication Data

US 2021/0298959 A1    Sep. 30, 2021

(51) Int. Cl.
| | | |
|---|---|---|
| *A42B 7/00* | (2006.01) |
| *A61F 9/04* | (2006.01) |
| *A42B 1/247* | (2021.01) |
| *A42B 1/041* | (2021.01) |

(52) U.S. Cl.
CPC ............ *A61F 9/045* (2013.01); *A42B 1/041* (2013.01); *A42B 1/247* (2013.01); *A42B 7/00* (2013.01)

(58) Field of Classification Search
CPC ........... A42B 1/041; A42B 1/247; A42B 7/00; A42B 1/04; A42B 1/018; A61F 9/045
USPC .......... 2/10, 171, 171.2, 173, 174, 202, 206, 2/207, 209.13, 209.14
See application file for complete search history.

(56) References Cited

U.S. PATENT DOCUMENTS

| | | | | |
|---|---|---|---|---|
| 2003/0193644 A1* | 10/2003 | Schwebel | .............. | A42B 1/247 351/62 |
| 2004/0148683 A1* | 8/2004 | Lindaman | ............ | A42B 1/0187 2/207 |
| 2006/0242751 A1* | 11/2006 | Koo | ........................ | A42B 1/247 2/171 |
| 2013/0315685 A1* | 11/2013 | Pedersen | ................. | F03D 13/40 410/44 |
| 2014/0304887 A1* | 10/2014 | Ilges | .................... | A42B 1/0186 2/172 |
| 2015/0150226 A1* | 6/2015 | McLeod | ................ | A01K 85/01 43/42.06 |
| 2019/0021430 A1* | 1/2019 | Elliott | ..................... | A61F 9/045 |
| 2019/0174855 A1* | 6/2019 | D'ambrosio | ......... | A42B 1/0185 |
| 2020/0390177 A1* | 12/2020 | Garmon | ................. | A42B 1/018 |

* cited by examiner

Primary Examiner — Gloria M Hale (57) ABSTRACT

A zipper pouch integrally forming a sleeping mask enclosing a retractable beanie. The zipper pouch is comprising a top surface and a rear surface, a retractable beanie having a front surface, a rear surface, and two side surfaces; wherein a front surface of the sleeping mask pouch aligns with and joins to two triangular points on each side of the pouch. The inseam copper wire on the inside front surface of the pouch in conjunction with the pull of the beanie is what creates a comfortable fit blocking out light and covering the users head. The zipper mask pouch is compact as it stows the beanie inside by rolling it back into the pouch and fastening it with a zipper.

19 Claims, 13 Drawing Sheets

ZIPPER POUCH WITH INTEGRATED MOLDABLE SLEEPING MASK AND RETRACTABLE BEANIE

BACKGROUND

The present invention relates generally to the field of sleeping masks, and more particularly to a zipper pouch with integrated sleeping mask and retractable beanie.

BRIEF SUMMARY

Embodiments of the present invention disclose a zipper pouch with an integrated sleeping mask and retractable beanie having a wear-mode for wearing and a storage mode for compact storage. The pouch that turns into the sleeping mask has a top seam, a bottom seam, two side seams, and a fastening mechanism located in a vicinity of the top seam to form an internal pouch formed at least in part by the sleeping mask. The retractable beanie is integrated with the sleeping mask shaped pouch, and aligns with and attaches to the sleeping mask in a vicinity of the top seam of the sleeping mask. In a wear-mode the retractable beanie is worn on the head of the user and the sleeping mask is folded down over a portion of a facial region of the user, or folded up onto the head of the user. In a storage mode the retractable beanie retracts into the internal pouch internal to the sleeping mask and is secured within the internal pouch by fastening the fastening mechanism. In various embodiments of the invention, the beanie may host fixtures such as buttons, snaps or VELCRO, hook and loop fastener, to hang surgical masks or face covering to protect from spread of virus. In various embodiments of the invention, the sleeping mask is strapless and is secured to the user's head in the wear-mode by wearing the retractable beanie. In various embodiments of the invention, the sleeping mask and retractable beanie may be formed from cotton, spun bamboo, nylon, silk, or any other type of cloth. The fastening mechanism, in various embodiments of the invention, may be one or more zippers of different weights, buttons, latches, threads for tying, etc. The sleeping mask may, in various embodiments of the invention, possess an inseam wire to mold the sleeping mask to one or more facial features of the user. The inseam wire may be formed from copper, aluminum, plastic, or any other material.

BRIEF DESCRIPTION OF THE DRAWINGS

FIG. 3 is showing the placement of the copper wire strip 102 with stitching around it 103. It is placed a half inch to the bottom of the sleeping mask cut out of 100. There may be a necessity for the strip to be placed in a custom-made sleeve depending of the type fabric used to compile the mask layers.

DETAILED DESCRIPTION

Sleeping masks provide a dark environment to shade the user's eyes during periods of sleep from bright light which may disturb the user's sleep. Presently, existing sleeping masks might not be comfortable because they are typically secured by a band that keeps the sleeping mask fastened to the user's face. Conventional sleeping masks may also serve to shut out light, but lack the ability to shut out other elements of the environment such as air-conditioning, drafts, background noise, as well as germs which may be present on seats and/or headrests existing in public transportation such as planes and trains. A beanie hat (hereinafter "beanie") offers the benefits of protecting one's hair and head from an environment such as a headrest on a plane or train, but do not offer the advantages of sleeping masks to shade one's eyes when used during sleep. Presently, there is no compact solution to reap the benefits of both a beanie and conventional sleeping mask at the same time, comfortably, and there is also no compact manner of storing the two. The present invention seeks to provide a solution to this problem by blending a beanie with a sleeping mask to provide the advantages of both to the user in not only including an environment such as a plane or a train, but also in any other environment the user desires to use the invention.

Figure 8:
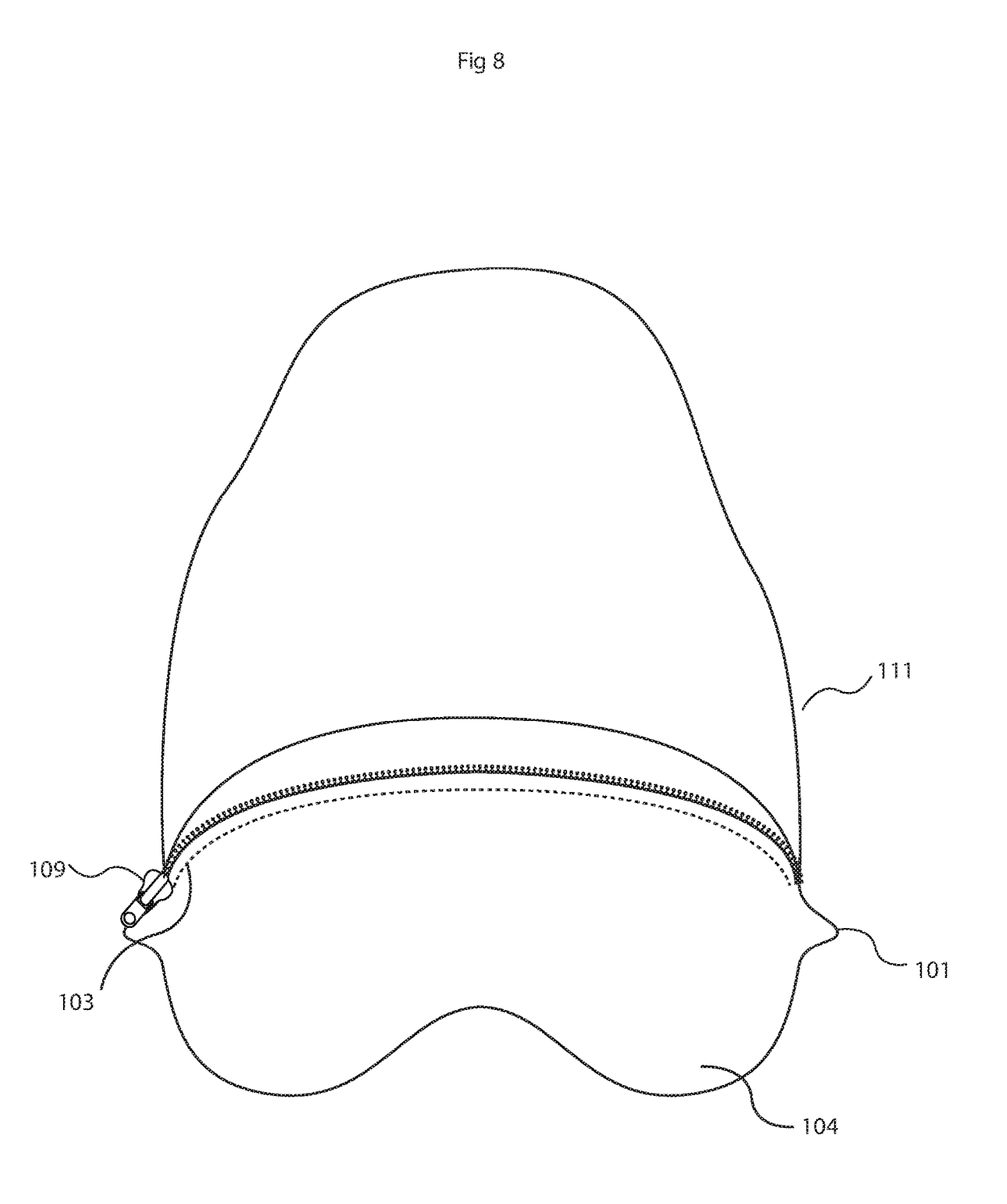
FIG. 8 is showing the beanie placement to the inside surface of 104a under the fastening mechanism 109 and attaching one side of the rim of the beanie to each corner 111 with a stitch 103 to the triangular tips 101 leaving the back of the hat open for the user to put on and so the pouch 110 aligns to the users face.
Figure 9:
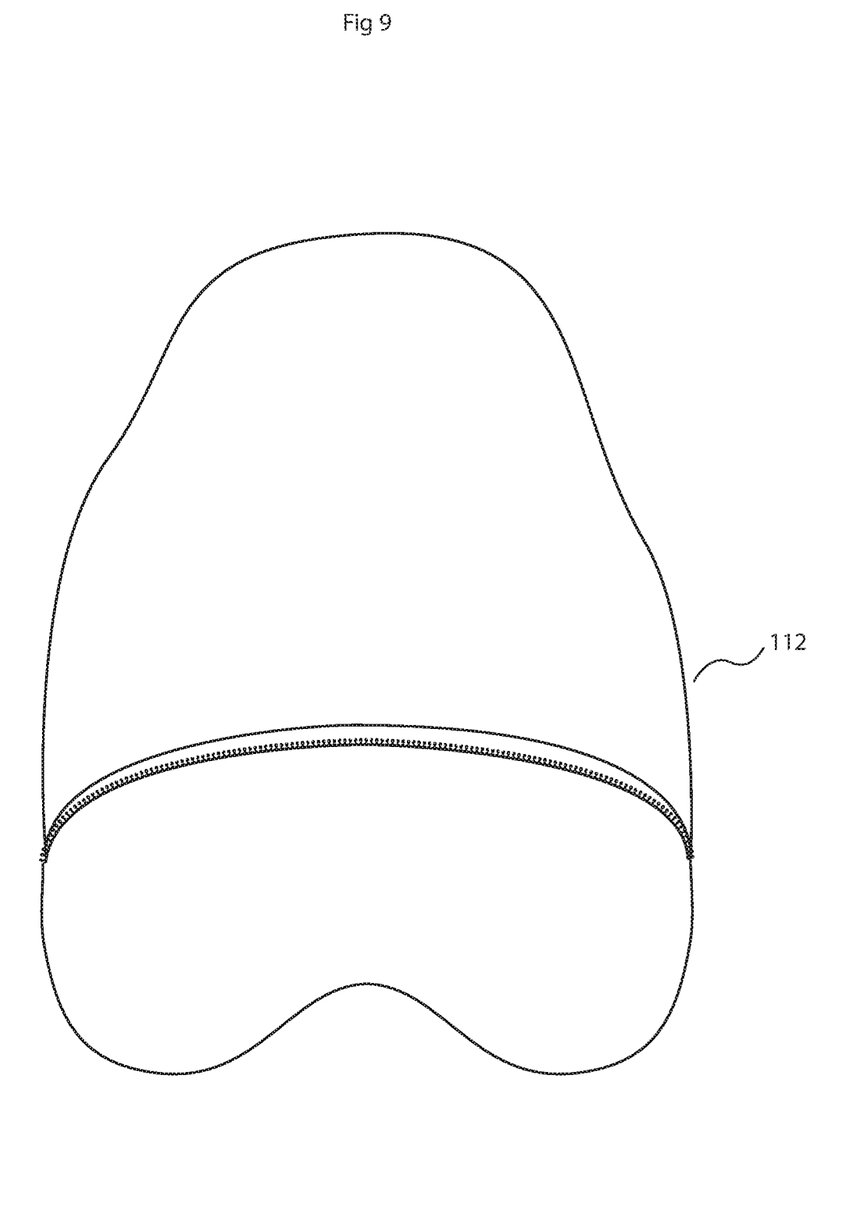
FIG. 9 is a front view of the mask and beanie attached 112.
Figure 10:
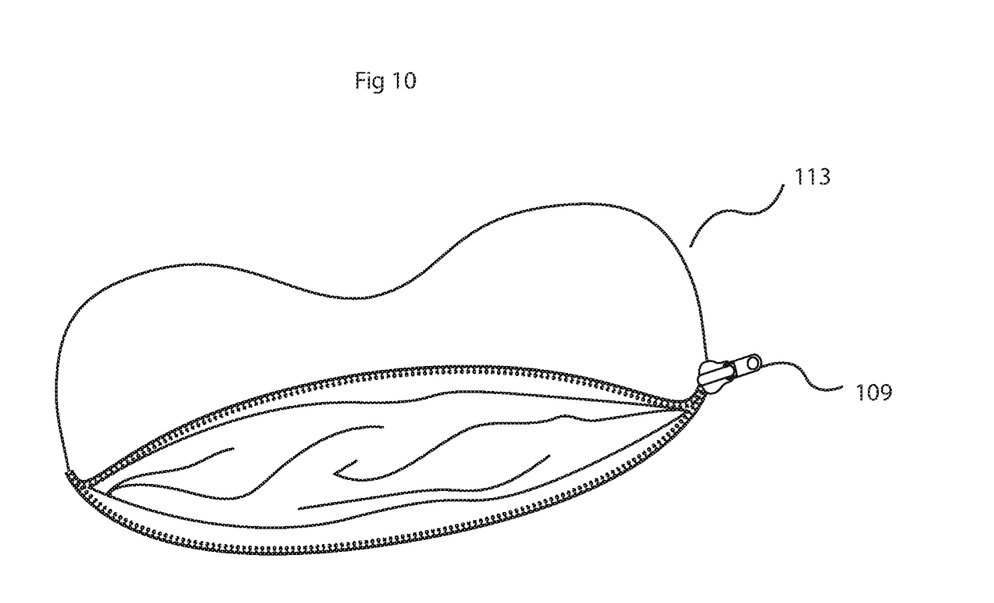
FIG. 10 is showing the beanie fully collapsed into storage mode with an unzipped pouch 113.
Figure 11:
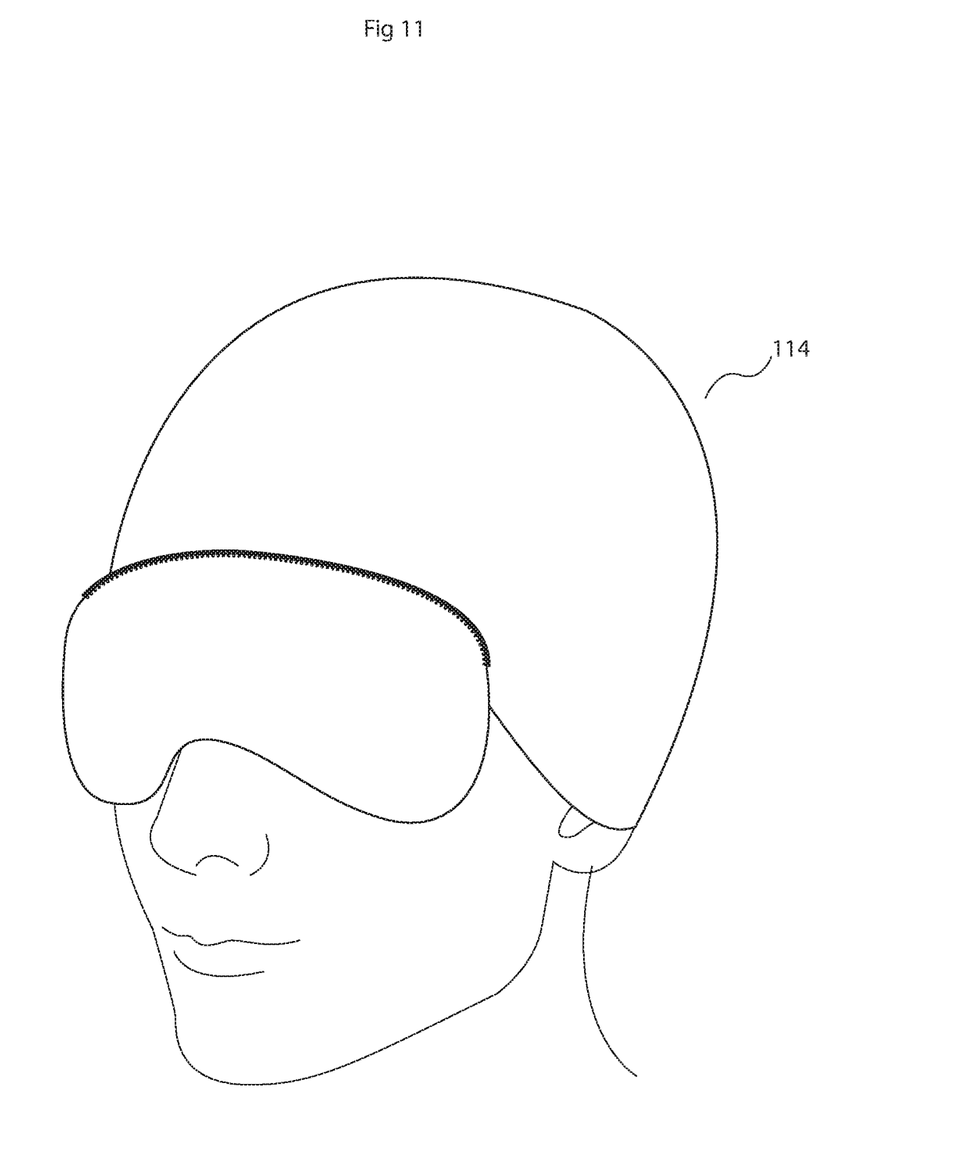
FIG. 11 is showing the beanie ensue with the zipper mask sleep pouch molded to the bridge of the users nose using the inseam copper wire and snug fit of the beanie 114.
Figure 12:
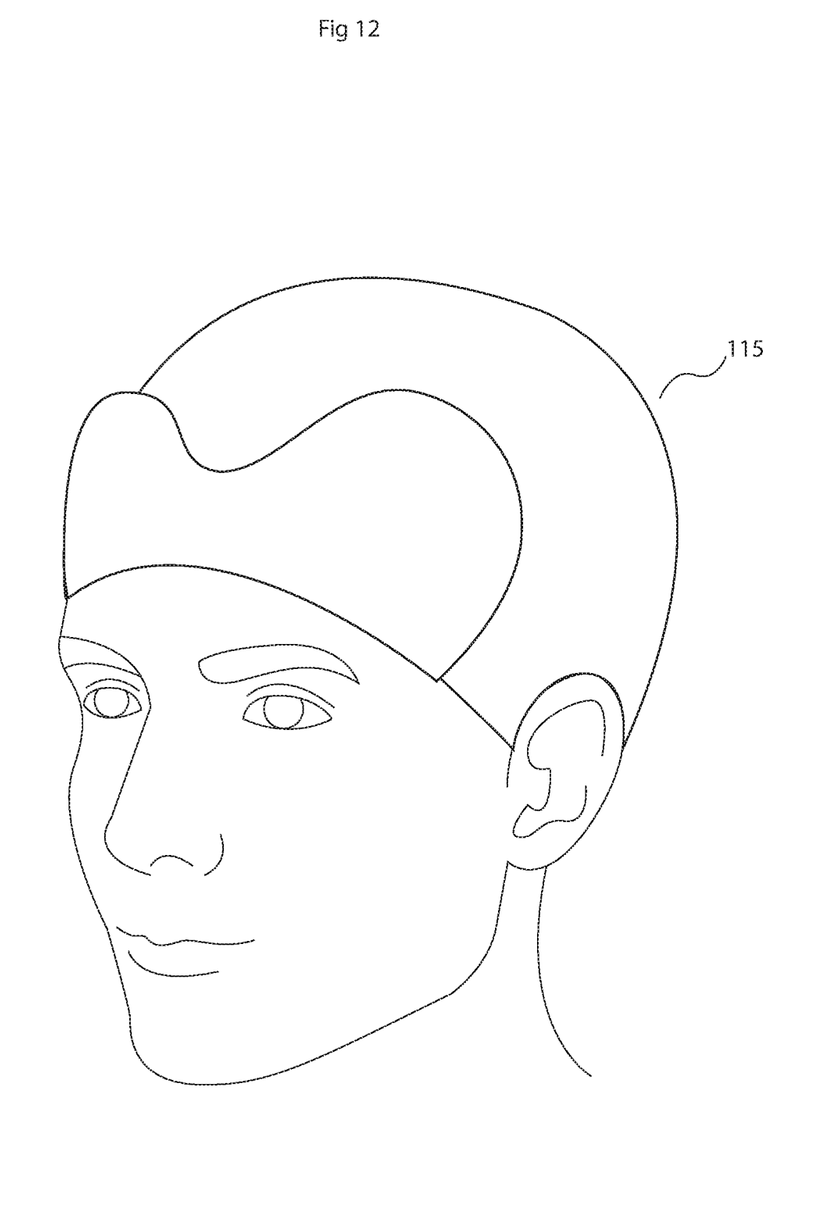
FIG. 12 is showing the sleep mask flipped up on the user's forehead 115.

The present invention offers a sleeping mask shaped zipper pouch with an integrated sleep mask and retractable beanie. The sleeping mask has a top seam, a bottom seam, and two side seams integrated with a front surface of a retractable beanie, to offer the user all the advantages of using a sleeping mask while sleeping. In various embodiments of the invention, the integrated retractable beanie may have attached VELCRO, hook and loop fastener, buttons or snaps at the ears for ease of attaching facemasks. The front side of the pouch that is the sleeping mask is in a vicinity of the top seam of the sleeping mask FIG. 8. In a storage mode, the retractable beanie retracts into the sleeping mask pouch and is closable with a fastening mechanism which secures the newly formed sleeping mask pouch FIG. 10. In a wear-mode, the retractable beanie is worn on the head of the user and the sleeping mask is folded down over a portion of a facial region of the user, or folded up onto the head of the user FIG. 11 and FIG. 12.

Figure 13:
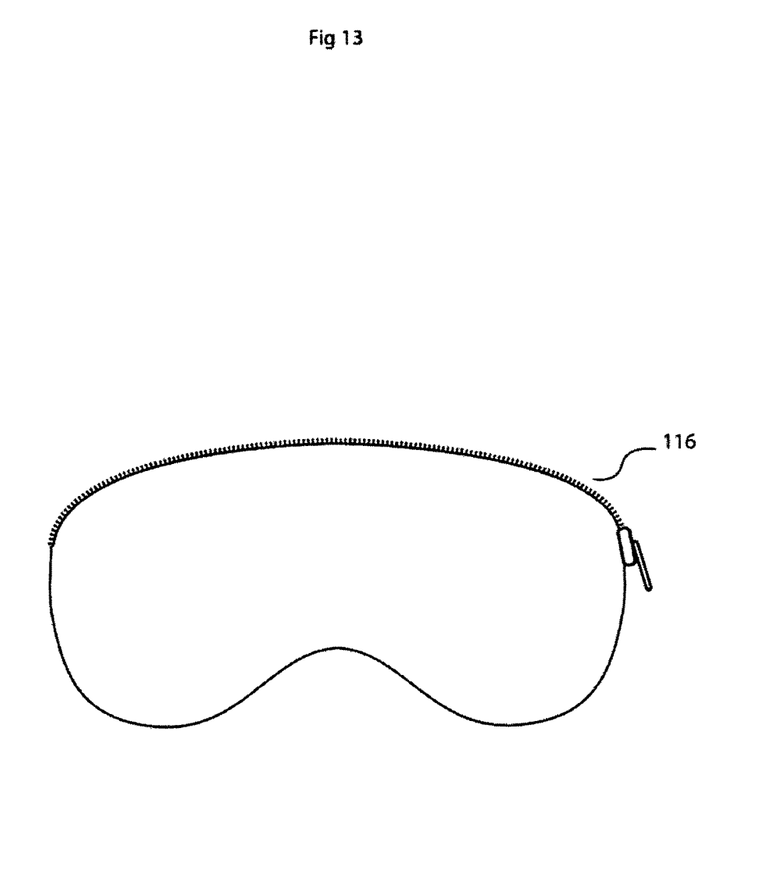
FIG. 13 Is showing the zipper pouch fully zipped up and in storage mode 116.

In an embodiment of the invention, the zipper pouch is shaped like a sleeping mask 110. The pouch stores an attached beanie from the inside and connects from each tip of the inside of the mask which is resting at the users temples creating a comforting and snug fit for both the rim of the beanie and the entire portion of the sleeping mask. The pouch unzips, and the user takes out the beanie and puts it on their head. The pouch portion is aligned over the face and pulled down over the eyes. Some embodiments of the invention may include a fixture such as VELCRO, hook and loop fastener, snaps or buttons to hang surgical and protective face masks for spread of viruses on the sides of the beanie near the ears. The flexible copper wire that is built into the bridge of the mask is pressed toward the bridge of the nose and molded for a snug fit and to shut out light like a proper sleeping mask FIG. 11. The mask flips up when the user only wants the hat to be in use FIG. 12. The user may take off the hat and put it back into the pouch FIG. 13. They may choose to store small objects in the pouch like a regular zipper case.

Figure 2:
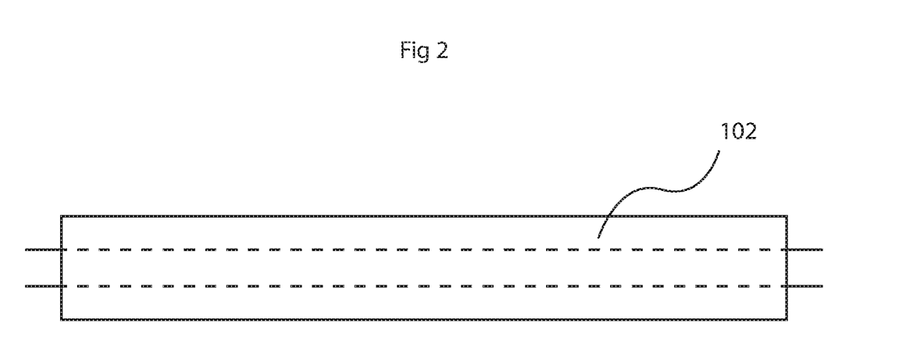
FIG. 2 is a flexible copper wire molding strip 102.
Figure 3:
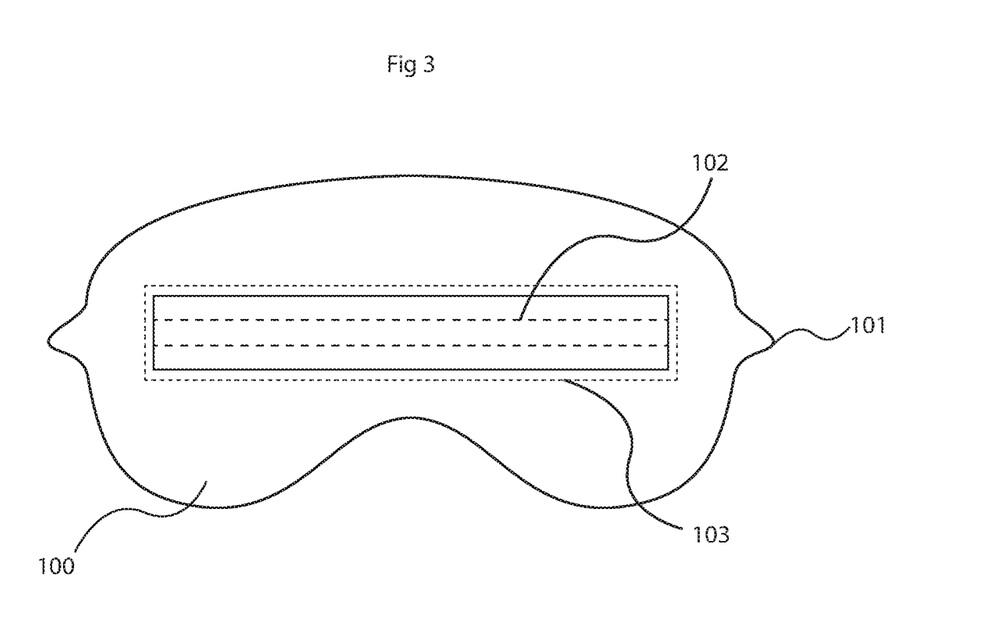
Figure 4:
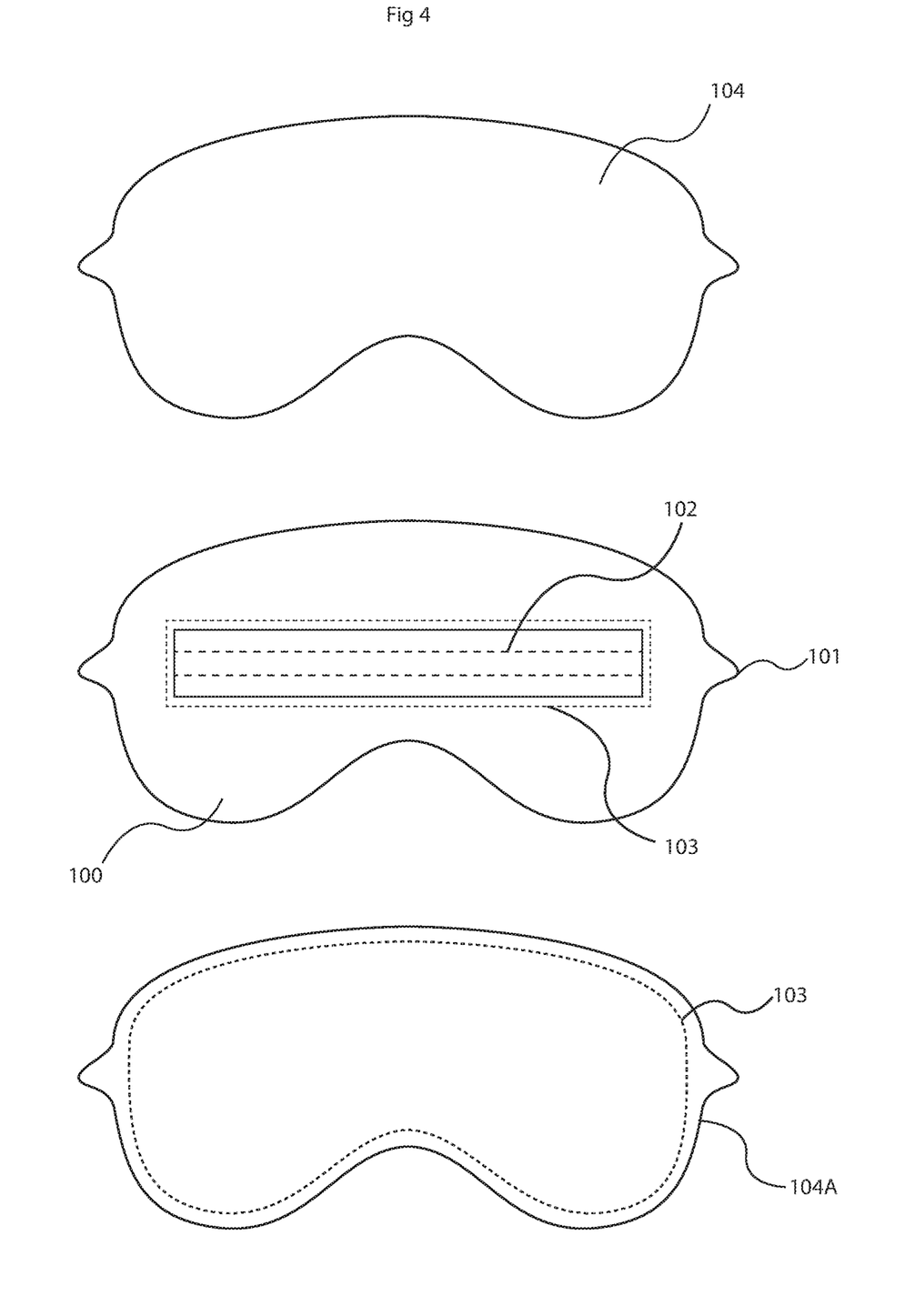
FIG. 4 is showing an identical cut out fabric layer of the mask pouch 104 being placed on top of the fabric layer 100 and stitched around the entire circumference of the mask about one quarter of an inch for the seam 103 result being 104A.
Figure 5:
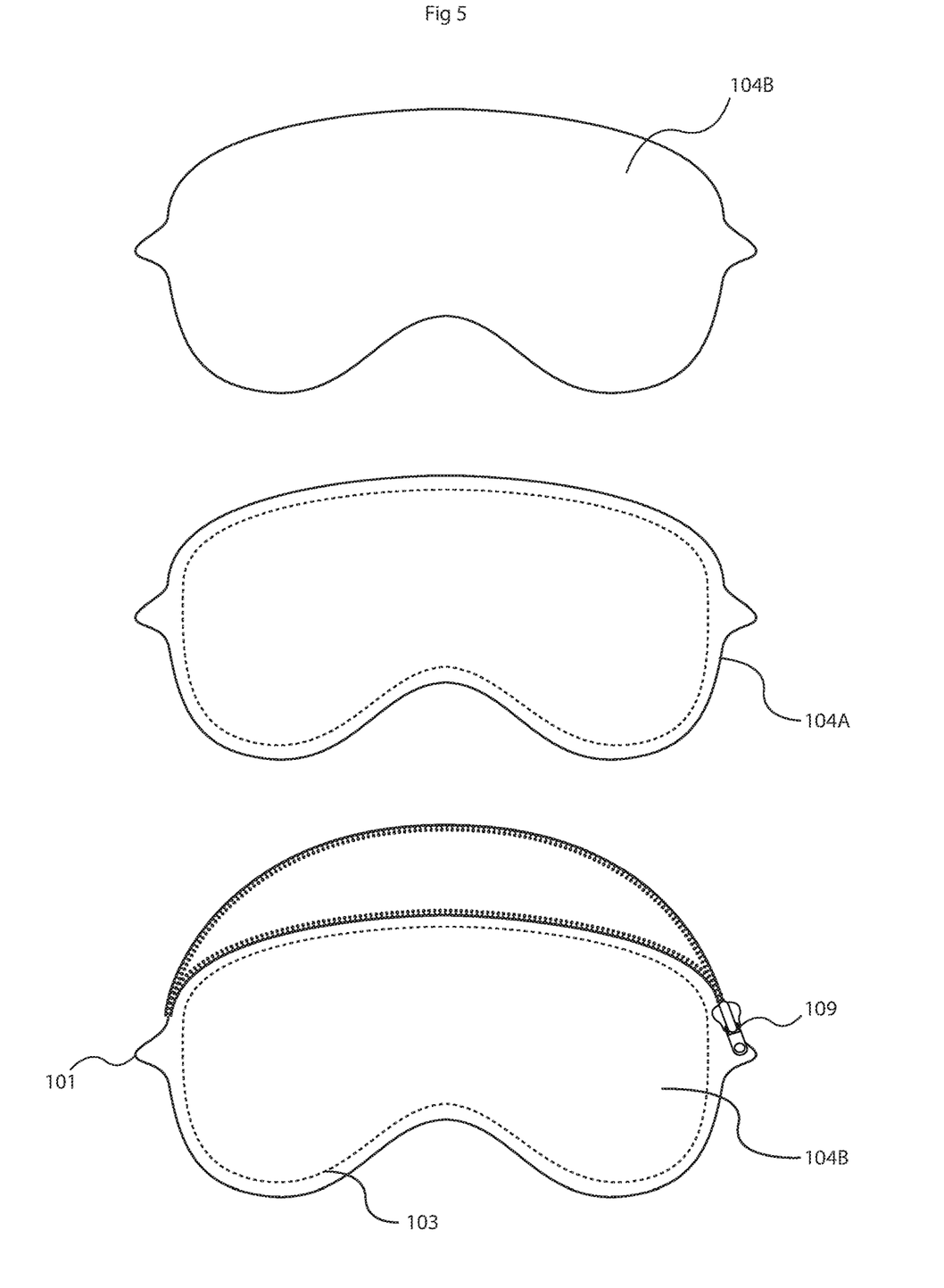
FIG. 5 is the continuation of making the pouch by placing another identical fabric layer 104B of the cut out mask shape attached to 104A using a stitch 103 halfway of the mask at the bottom and stopping at two triangle tips sticking out on each side 101. 109 is the fastening mechanism used to close and open the pouch attaching to each triangular point 101 and sewn using a stitch 103 to the top portion of the mask and to each side of 104A and 104B forming a pouch.
Figure 6:
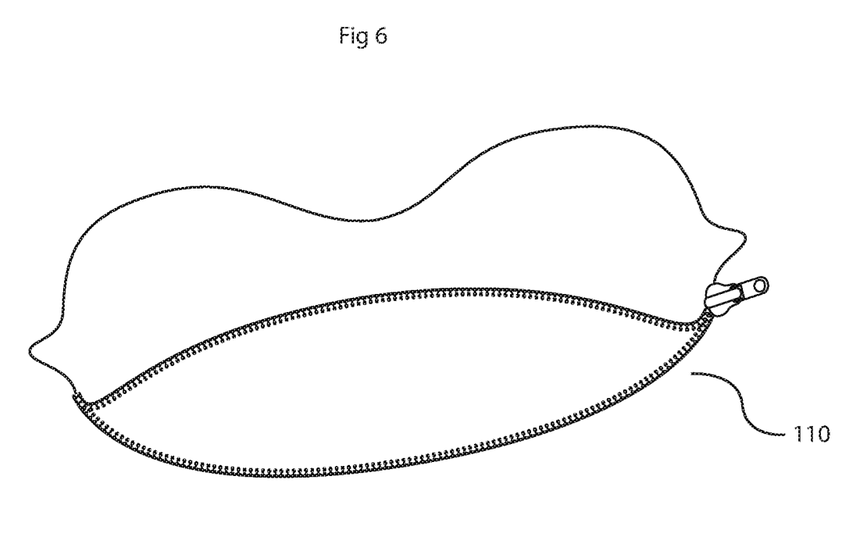
FIG. 6 is the view of the completed mask pouch when flipped right side-in, in storage mode tucking away the points for a smooth looking mask 110.
Figure 7:
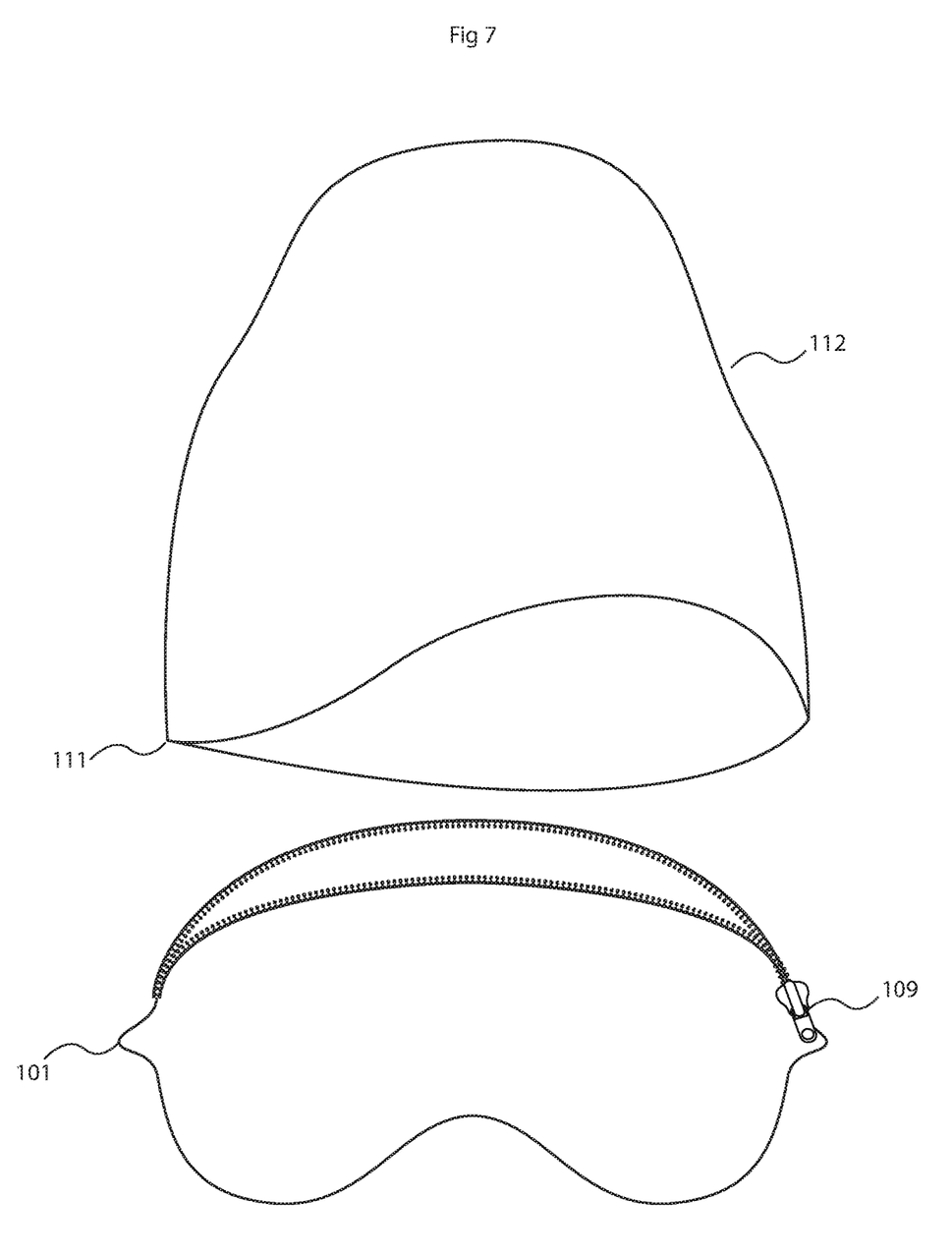
FIG. 7 is showing the Beanie 112 head covering using bamboo fabric or other organic, temperature controlling fabrics assembled for the user's head and to be placed into the mask. The beanies are form fitting but not too tight. 111 is the points on the rim of the beanie that will connect to the mask's triangular points on the outer edges 101.

In an embodiment of the invention, the pouch has a sleeping mask portion that is equipped with an inseam copper wire so that the mask is moldable to the users bridge of their nose FIG. 2. The components can be used all at once to shut out light, or the user is able to flip up the sleeping mask to use the beanie only. The zipper pouch that is also the sleeping mask, stores the beanie compactly and becomes a case to carry other small items such as identity card, keys, chapstick, ear-pods, essential oils for aromatherapy. Some models may have an inseam pocket in the pouch for credit cards and id cards making the zipper pouch also a wallet.

The present invention offers the advantage of elimination of a conventional sleeping mask strap which is typically used with sleeping masks used to fasten the sleeping mask to the user's head. The beanie, in the presently disclosed invention, replaces the mask strap in fastening the presently disclosed invention to the user's head when in use. This provides for a more comfortable fit. The presently disclosed invention covering the ears and compact use for those who want a head covering. The snug fit in combination with the sleeping mask acts as a more effective sleeping aid. The environment that is created by using the apparatus is therapeutic.

Preferred Aspects:

Preferably The mask is a pouch with a zipper that enables the beanie to be stored as well as the flexible copper wire sewn into the bridge of the mask. The intent of the zipper pouch is to give a place for the beanie in a compact stylish way giving this multiple use as a sleep-mask with beanie and carry case.

The invention is an improvement on prior wearable sleeping aids as it helps the user have the comfort of the conventional sleeping mask with the addition of the soft beanie for optimal comfort and quality sleep. The moldable face mask fits every person's face while using the beanie. They have the option to flip up the mask if they do not want to have their eyes covered, and it will still look very stylish.

Other methods used previously are not complete, compact and face moldable. Existing features from prior art are not packaged or multi use. For example, a beanie that covers the entire head up to the nose in a snug fashion is not an attractive and compact invention and may be too snug for some users and you cannot remove one part of the product without taking the entire thing off. Another example, the conventional sleeping mask, this is just a hanging product, it cannot be packed away, there is no added comfort of the sleeping mask with a secure molding to the face, it is simply covering the light out. The hooded neck pillow is whereas trying to cover the head and eyes at the same time, it is not a full idea.

No previous invention is able to be this compact embodying the two elements while being totally moldable to the face.

They do not complete the idea of having a stylish, compact and very comfortable way of wearing a sleeping mask with the added comfort of a beanie. There is no easy way to store these items.

The invention improves on them by combining and compacting the four elements. Sleeping mask, beanie, moldable sleeping mask and zipper pouch to store the hat. Giving it a multifunctional and compact use. You can use it as a sleeping mask head covering, a head covering, a pouch to store small personal items.

The invention can be used as a small wallet to carry chapstick, earbuds, headphones, credit cards, keys, id.

The materials needed to make the invention requires a custom size cut beanie to fit the meeting points of the zipper mask, in the standard fashion of making the beanie or skull cap. Three to five cut outs of the sleeping mask/pouch pattern depending on material. Always two or three for the portion that holds the inseam wire and either one or two layers for the back portion of the pouch eye mask. A zipper, Bias tape for inseam shape holding, a doubled and flexible copper wire strip and thread.

Figure 1:
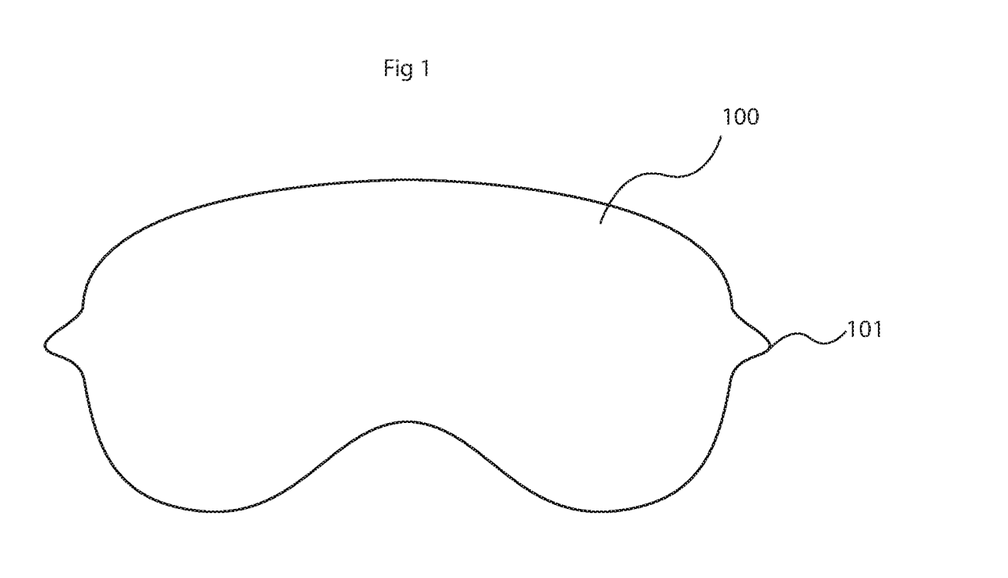
FIG. 1 is a piece of fabric cut into the shape of a sleep-mask shape 100 with two points extending out on the half-way points of the outer edges 101.

The cut out of the eye mask has two points on the outside edges at the midpoint on the left and right FIG. 1. The portion of the pouch that hosts the flexible copper wire gets the first stitch to the bridge of the mask. There is a layer of a mask cutout that covers the copper wire and stitched together around the entire circumference. The back portion of the pouch is stitched to the front portion pouch. Halfway at the points mentioned in the first line. The bias tape is applied to the bottom of the mask and stitched together holding the mask shape Fig. The zipper is sewn to the top opening of the mask to both the front and back and extends only to the two said points from the cutouts. Next, the front rim of the beanie is attached to the front inside portion of the mask at the top inside surface to the portion of the mask that hosts the inseam copper wire strip and stitched together from each of the triangular points.

What is claimed is:

1. A sleeping mask having an integral sleeping mask shaped storage pouch with an integrated retractable beanie in combination, comprising:

a sleeping mask configured to at least cover a user's eyes and nose bridge for covering said user's eyes thereby producing an environment conducive for sleeping;

said sleeping mask formed of at least two material layers wherein the sleeping mask front surface is integrally formed with a front surface of the integrated retractable beanie, wherein when said beanie is worn on a user said sleeping mask extends downwardly from said beanie to cover said user's eyes thereby providing said conducive sleeping environment in a sleeping mode;

and wherein when said user is not wearing said beanie and integrated sleeping mask, said beanie is retracted into said pouch formed by said two material layers having a closeable opening securely sealed with a fastener integral with a top surface of one of said two sleeping mask layers whereby when said beanie is retracted into said mask shaped sleeping pouch in a storage mode said integral beanie is stored and secured within said pouch.

2. The sleeping mask as claimed in claim 1 and further wherein said sleeping mask and said retractable beanie are formed from any of cotton, nylon, silk, spun bamboo or organic temperature controlling fabric layers.

3. The sleeping mask as claimed in claim 1 and further wherein said sleeping mask fastening mechanism is any one of a zipper, one or more buttons, latches or tying threads.

4. The sleeping mask as claimed in claim 1 and further wherein the sleeping mask includes an inseam having a copper wire to mold the sleeping mask to one or more facial features of the user.

5. The sleeping mask as claimed in claim 1 wherein said integrated retractable beanie includes hook and loop fasteners, buttons or snaps configured to be located at a user's left and right ear locations for attaching a user's facemask to said beanie as desired.

6. The sleeping mask as claimed in claim 1 wherein said sleeping mask pouch is configured to hold said beanie therein as well as any other user items including credit cards, earbuds, headphones, lip treatment sticks, identification cards, keys or any other small consumer item therein.

7. The sleeping mask as claimed in claim 1 wherein said beanie is configured to be form fitting on a user head.

8. A method of making a sleeping mask having an integral sleeping mask shaped storage pouch with an integrated retractable beanie in combination, comprising:
cutting two material fabric layers shaped in a shape of a sleeping mask configured to cover a user's eyes and nose bridge thereby producing an environment conducive for sleeping;
adding at least one strip of copper wire and a fabric strip for placement over said copper wire to thereby sew said copper wire to said sleeping mask about an area that is configured to overlie a bridge of a user's nose to secure said mask on said user's nose during sleeping;
providing a form fitting fabric beanie configured to surround a user's head;
sewing a bottom seam and two side seams about said two layers of said sleeping mask material fabric layers and leaving said top seam open to sew therein a fastening mechanism to create an openable and closeable opening;
sewing a bottom rim of said beanie to a top seam of one of said sleeping mask layers to secure said beanie to said sleeping mask one layer and wherein said seam formed between said beanie and said sleeping mask connects said beanie to said sleeping mask and allows said beanie to be folded downwardly into said sleeping mask pouch formed by said two sleeping mask layers and said fastening mechanism and wherein said fastening mechanism is closeable after said beanie is folded within said sleeping mask pouch for said storage mode.

9. A method of making a sleeping mask having an integral sleeping mask shaped storage pouch with an integrated retractable beanie in combination as claimed in claim 8 and further comprising:
attaching any of hook and loop fasteners, buttons or snaps configured to be located at a user's left and right ear locations for attaching a user's facemask to said beanie as desired.

10. A method of making a sleeping mask having an integral sleeping mask shaped storage pouch with an integrated retractable beanie in combination as claimed in claim 8 and further comprising:
wherein said sleeping mask and said retractable beanie are formed from any of cotton, nylon, silk, spun bamboo or organic temperature controlling fabric layers.

11. A method of making a sleeping mask having an integral sleeping mask shaped storage pouch with an integrated retractable beanie in combination as claimed in claim 8 and further comprising:
wherein said sleeping mask fastening mechanism is any one of a zipper, one or more buttons, latches or tying threads.

12. A method of making a sleeping mask having an integral sleeping mask shaped storage pouch with an integrated retractable beanie in combination as claimed in claim 8 and further comprising:
wherein said sleeping mask pouch is configured to hold said beanie therein as well as other user items including any of credit cards, earbuds, headphones, lip treatment sticks, identification cards, keys or any other small item therein.

13. A method of providing an environment conducive for sleeping, comprising:
providing a sleeping mask having an integral sleeping mask shaped storage pouch with an integrated retractable beanie in combination as claimed above in claim 1;
said sleeping mask configured to at least cover a user's eyes and nose bridge for covering said user's eyes thereby producing an environment conducive for sleeping;
placing said sleeping mask, sleeping mask shaped pouch and retractable beanie on a user's head wherein said beanie snuggly fits said user's head in a form fitting fashion and said sleeping mask is folded downwardly over eyes of said user to cover said users eyes and wherein said copper wire configured to lie over a user's bridge is form fitted and pressed on said user's nose bridge to secure said sleeping mask on said user to cover said user's eyes in a way that is conducive for sleeping.

14. The method of providing an environment conducive for sleeping as claimed in claim 13 and further comprising:
wherein when said user is not wearing said beanie and integrated sleeping mask, said beanie is retracted into said pouch formed by said two material layers having a closeable opening securely sealed with a fastener integral with a top surface of one of said two sleeping mask layers whereby when said beanie is retracted into said mask shaped sleeping pouch in a storage mode said integral beanie is stored and secured within said pouch.

15. The method of providing an environment conducive for sleeping as claimed in claim 13 and further comprising:
wherein said sleeping mask and said retractable beanie are formed from any of cotton, nylon, silk, spun bamboo or organic temperature controlling fabric layers.

16. The method of providing an environment conducive for sleeping as claimed in claim 13 and further comprising:
wherein said sleeping mask fastening mechanism is any one of a zipper, one or more buttons, latches or tying threads.

17. The method of providing an environment conducive for sleeping as claimed in claim 13 and further comprising:

wherein the sleeping mask includes an inseam having a copper wire to mold the sleeping mask to one or more facial features of the user.

18. The method of providing an environment conducive for sleeping as claimed in claim 13 and further comprising:
wherein said integrated retractable beanie includes any of hook and loop fasteners, buttons or snaps configured to be located at a user's left and right ear locations for attaching a user's facemask to said beanie as desired.

19. The method of providing an environment conducive for sleeping as claimed in claim 13 and further comprising:
wherein said sleeping mask pouch is configured to hold said beanie therein as well as other user items including any of credit cards, earbuds, headphones, lip treatment sticks, identification cards, keys or any other small item therein.

\* \* \* \* \*